(12) United States Patent
Baumann et al.

(10) Patent No.: US 10,660,594 B2
(45) Date of Patent: May 26, 2020

(54) EXAMINATION AND/OR TREATMENT DEVICE COMPRISING A MULTI-AXIS ROBOT

(71) Applicant: Siemens Healthcare GmbH, Erlangen (DE)

(72) Inventors: Berthold Baumann, Kastl (DE); Robert Divoky, Forchheim (DE); Franz Fadler, Hetzles (DE); Stefan Gross, Kirchenthumbach (DE); Norbert Herrmann, Ebnath (DE); Matthias Hoff, Marktredwitz (DE); Michael Ott, Speinshart (DE); Volker Rose, Bayreuth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 50 days.

(21) Appl. No.: 16/044,699

(22) Filed: Jul. 25, 2018

(65) Prior Publication Data
US 2019/0029620 A1 Jan. 31, 2019

(30) Foreign Application Priority Data
Jul. 28, 2017 (DE) ........................ 10 2017 213 033

(51) Int. Cl.
*A61B 6/00* (2006.01)
*B25J 19/00* (2006.01)
*B25J 11/00* (2006.01)
*B25J 18/00* (2006.01)
*H02G 11/00* (2006.01)

(52) U.S. Cl.
CPC .......... *A61B 6/4458* (2013.01); *A61B 6/4441* (2013.01); *B25J 11/008* (2013.01); *B25J 18/00* (2013.01); *B25J 19/0025* (2013.01); *H02G 11/00* (2013.01)

(58) Field of Classification Search
CPC .............................. A61B 6/4458; H02G 11/00
See application file for complete search history.

(56) References Cited

U.S. PATENT DOCUMENTS

| | | | |
|---|---|---|---|
| 2007/0165786 A1* | 7/2007 | Grasser | A61B 6/56 378/194 |
| 2009/0147924 A1* | 6/2009 | Gross | A61B 6/4441 378/194 |

FOREIGN PATENT DOCUMENTS

DE 102015201829 A1 1/2016

* cited by examiner

*Primary Examiner* — Dani Fox
(74) *Attorney, Agent, or Firm* — Harness, Dickey & Pierce, P.L.C.

(57) ABSTRACT

An examination and/or treatment device includes a multi-axis robot having an articulated arm that can be moved in space as well as leads received in a flexible cladding tube and guided to one or more examination or treatment devices arranged on the articulated arm or a support arranged thereon. In an embodiment, on the articulated arm is provided a carriage arrangement including a carriage, having at least one deflection roller and that can be linearly displaced against at least one restoring element that builds up a restoring force. The cladding tube or a guide tube surrounding the cladding tube is guided around the deflection roller.

22 Claims, 4 Drawing Sheets

EXAMINATION AND/OR TREATMENT DEVICE COMPRISING A MULTI-AXIS ROBOT

PRIORITY STATEMENT

The present application hereby claims priority under 35 U.S.C. § 119 to German patent application number DE 102017213033.4 filed Jul. 28, 2017, the entire contents of which are hereby incorporated herein by reference.

FIELD

At least one embodiment of the invention generally relates to an examination and/or treatment device comprising a multi-axis robot having an articulated arm that can moved in space as well as leads received in a flexible cladding tube and guided to one or more examination or treatment devices arranged on the articulated arm or a support arranged thereon.

BACKGROUND

Multi-axis robotic systems are increasingly being used in medical technology for examination and/or treatment devices, for example for imaging X-ray equipment. These comprise a multi-axis robot having an articulated arm that can be moved in space, wherein the multi-axis robot conventionally has a base frame arranged on the floor, on which a multi-arm construction comprising at least two arms that can be pivoted relative to each other is arranged, wherein the multi-arm construction is arranged on the base frame so as to be rotatable about a vertical axis. A support is usually arranged on the robot arm and can be moved on the arm about one or more axes, so, overall, a robotic movement device having usually six axes of movement results.

Often arranged on the articulated arm, in the region for example of the imaging systems, is a C-arm as a support, which C-arm can move on the articulated arm either along an orbital path or along a linear guide and can conventionally also be rotated about an axis. Usually arranged on this C-arm in this case is a radiation source and a radiation receiver, for example an X-ray emitter and an X-ray radiation receiver. These examination or treatment devices are connected to appropriate leads in order to supply them accordingly, be it with current, be it optionally for cooling, etc., but also in order to transmit corresponding control signals or to convey measurement signals to an associated control and/or processing device. Owing to the high level of mobility in space of the support or of the examination and/or treatment devices achieved by way of the multi-axis robot, an appropriate reserve of leads has to be kept in readiness so the leads can always be carried along independently of the movement. This means that the lead reservoir or cable reservoir has to designed in such a way that the requisite cable length or lead length can be provided in the clinically relevant repository.

It is known to assemble these separate lead stores in the ceiling so there is sufficient space on the floor to firstly carry out the necessary movements, but secondly also for example to be able to position the examination table, etc. Additional mechanical or mechatronic assemblies, such as a balancer, gas pressure springs or motor-assisted systems, etc. are integrated in a lead reservoir of this kind in the ceiling, and these are used to tension the leads, which are usually guided in a cladding tube, such as, for example a corrugated tube or a spiral tube, and to prevent loopings.

SUMMARY

The inventors have discovered that known lead storage systems assembled in the ceiling are complex and associated with high expenditure in terms of assembly and maintenance. In particular, additional ceiling fixings and/or suspensions have to be provided. Furthermore, a ceiling system of this kind is of course difficult to clean.

At least one embodiment of the invention is therefore based on the problem of specifying an improved examination and/or treatment device comprising a multi-axis robot.

At least one embodiment is directed to an examination and/or treatment device that, on the articulated arm, is provided a carriage arrangement comprising a carriage having at least one deflection roller and that can be linearly displaced against at least one restoring element that builds up a restoring force, wherein the cladding tube or a guide tube surrounding this is guided around the deflection roller.

BRIEF DESCRIPTION OF THE DRAWINGS

Further advantages and details of the present invention result from the example embodiments described below, and with reference to the drawings, in which.

DETAILED DESCRIPTION OF THE EXAMPLE EMBODIMENTS

Figure 1:
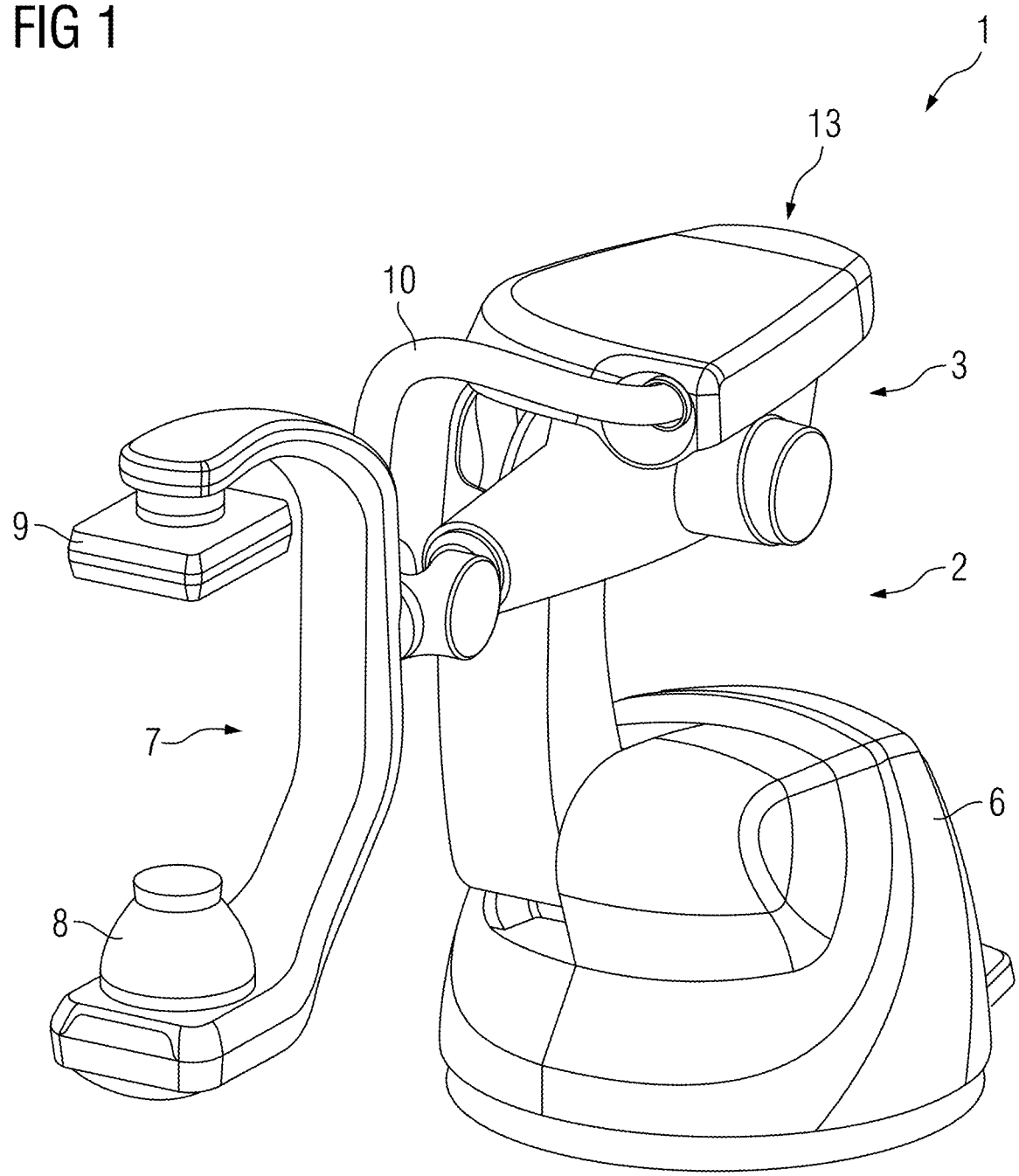
FIG. 1 shows a perspective view of an embodiment of an inventive examination and treatment device.

In the following, embodiments of the invention are described in detail with reference to the accompanying drawings. It is to be understood that the following description of the embodiments is given only for the purpose of illustration and is not to be taken in a limiting sense. It should be noted that the drawings are to be regarded as being schematic representations only, and elements in the drawings are not necessarily to scale with each other. Rather, the representation of the various elements is chosen such that their function and general purpose become apparent to a person skilled in the art.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment is directed to an examination and/or treatment device that, on the articulated arm, is provided a carriage arrangement comprising a carriage having at least one deflection roller and that can be linearly displaced against at least one restoring element that builds up a restoring force, wherein the cladding tube or a guide tube surrounding this is guided around the deflection roller.

It is inventively provided, in at least one embodiment, to arrange the lead store on the articulated arm itself. Provided on the articulated arm is a carriage arrangement, of course in an appropriate housing, to which the leads run and from which they are guided to the examination or treatment device(s), the arrangement comprising a linearly movable carriage, which can move against the restoring force of at least one restoring element.

Provided on the carriage is at least one deflection roller about which the cladding tube, in which the leads are guided at least from the lead store to the examination or treatment device(s), or a similarly flexible guide tube that surrounds this cladding tube is guided. The cladding tube and the guide tube respectively, and therewith the leads guided therein, are tensioned by way of this carriage and the restoring element. In other words, they are not loose and do not form a loop in space.

The required lead length can nevertheless be taken from the lead store by the articulated arm and the multi-axis robot respectively moving and positioning the examination or treatment devices accordingly. The required lead length is pulled from the lead store here, with the carriage being moved against the restoring element. If the examination or treatment device is moved into a different position again or back into the starting position, the carriage is pushed back by the restoring element but the cladding tube or the guide tube is also retracted again thereby into the lead store, in other words the corresponding housing arranged on the articulated arm.

According to at least one embodiment of the invention, the lead store is therefore integrated on the articulated arm itself, so a complex arrangement on the ceiling, etc. is not necessary. Furthermore, if the lead store can be moved in space by way of the articulated arm, it is therefore in turn also carried along, so ultimately the maximum cable length that need be taken therefrom is much shorter than in the case of permanent assembly in the ceiling. Owing to the arrangement on the articulated arm, the lead store is also straightforward to assemble as well as to maintain when a service is required, and it is also very easy to clean.

Even if it is already sufficient to provide just one deflection roller, of appropriately large dimensions, it is expedient to provide a plurality of deflection rollers on the carriage arranged along an arcuate path. These relatively small deflection rollers positioned on the arcuate path enable reliable guidance of the cladding tube or guide tube along the arcuate path. Kinking of the tube or excessive bending is avoided hereby and a correspondingly small radius can nevertheless be implemented.

The restoring element, which is actuated during a movement of the carriage, is preferably a spring element, for example in the form of a gas spring, a helical spring or a laminated disk spring, wherein a plurality of such springs can of course also be provided, in other words for example two parallel gas pressure springs or two parallel helical springs. The choice of the number of spring elements or their design is made according to the requirements during operation.

In a development of at least one embodiment of the invention, it can be provided that the carriage arrangement comprises a carriage holder on which at least one linear guide that guides the carriage is provided. This carriage holder is secured to the articulated arm; arranged on it is/are the restoring element(s) or spring element(s) as well, of course, as the carriage, which can move on the linear guide of the carriage holder. This results in a compact construction.

The restoring element(s) is/are firstly supported on the carriage holder and secondly on the carriage. In other words, they can easily be integrated accordingly in the carriage arrangement.

In order to prevent the carriage coming to an abrupt stop during movement of the examination or treatment device(s) into an end position, in which the carriage is also moved into its end position, which is limited by a stop, an expedient development of the invention provides resilient end stops in order to damp the movement of the carriage into an end position. These resilient end stops can be for example simple rubber buffers or the like, or damping springs, against which the carriage runs.

The articulated arm itself comprises at least two arms, namely a first arm movably connected to a base frame and a second arm pivotably connected to the first arm, wherein the carriage arrangement is arranged on the second arm. The first arm, as already described in the introduction, is conventionally rotatable about a vertical axis relative to the base frame, and pivotable about a horizontal axis. Pivotably mounted on the base frame is the second arm, which is provided for example with a coupling element, which can be turned about the arm longitudinal axis, and on which the support is then movably arranged. If the carriage arrangement is arranged on the second arm, then it can be moved with this arm. It is therefore located relatively close to the support, or rather the examination or treatment device(s), and this manifests itself in relatively short cable lengths.

In order to prevent the cables from rubbing against each other or for whatever reason from winding themselves around each other or being subject to tensile stress during the permanent movement of the articulated arm, and therewith also a permanent cable movement, an expedient development of the invention provides that the leads are received in a flexible, multi-membered energy chain, which runs through the cladding tube. This energy chain, which preferably has two or more separate chambers for receiving at least one lead, ensures that the leads are guided without excessive contact, but the requisite flexibility nevertheless remains. Excessive rubbing or the like is advantageously avoided hereby, so no drawbacks result from the arm movement, or rather the lead movement.

The energy chain can only be secured, with the end which faces the examination or treatment device(s) or the support, to the or an examination or treatment device or the support or a metal member protection chain connected thereto. It has proven to be sufficient to connect the energy chain with only the one, front end remote from the lead store to one of said articles because, owing to the, axially viewed, given sufficient inherent stability of the energy chain, which conventionally consists of a large number of separate chain members, which are articulated, in particular pivotably connected, to each other, additional securing with the second end is not necessary.

The support itself is preferably a C-arm, which is arranged on the articulated arm and is moved in space by this arm. The examination or treatment devices are expediently a radiation source and a radiation receiver, preferably based on X-rays.

FIG. 1 shows an embodiment of an inventive examination and/or treatment device 1, comprising a multi-axis robot 2 having an articulated arm 3 that can be moved in space, and in the illustrated example has at least two articulated arms 4, 5 connected together so as to be pivotable, wherein the articulated arm 4 is arranged on a base frame 6 so as to be pivotable and movable about a vertical axis. In the illustrated example a C-arm 7 is arranged on an articulated arm 3, and in turn supports a radiation source 8 and a radiation receiver 9. The C-arm 7 can be moved by way of the multi-axis robot 2 almost as desired.

Figure 4:
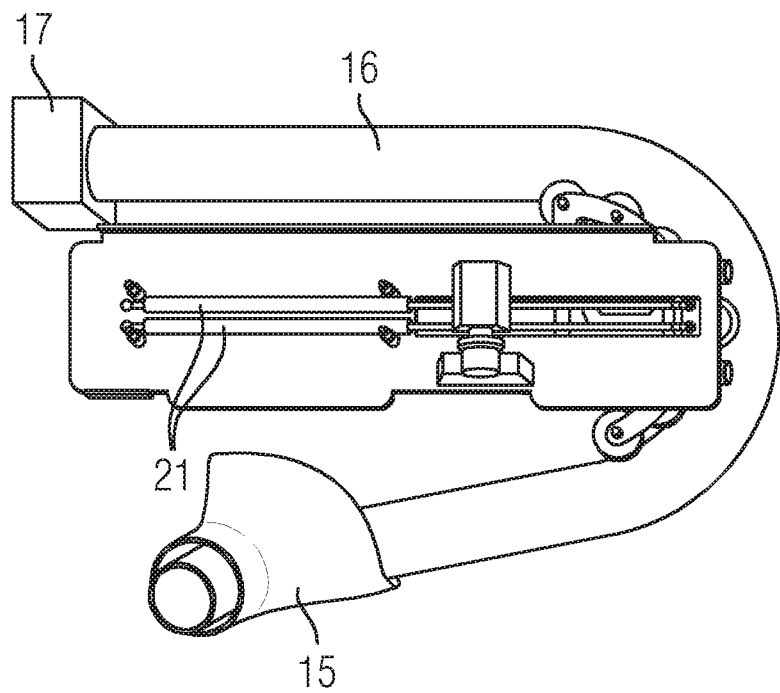
FIG. 4 shows a view of the arrangement from FIG. 3 from below.

To ensure operation of the device 1, a large number of leads is provided, which can be supply lines or signal lines, in other words cables, which are to be guided from a control and processing device (not shown) to the device 1 and there in particular to the radiation source 8 and the radiation receiver 9. These are conventionally received in a cladding tube 10, for example a corrugated or spiral tube, see also FIG. 2 in this regard, in that the leads are guided and received in an energy chain 12 having a large number of individual members 11 and having a plurality of continuous channels in which the leads are received, see FIG. 4 in this regard.

The cladding tube 10, including the energy chain 12 and therewith the leads (not shown), runs into a housing 13 in which a carriage arrangement 14 is provided, and out of this housing 13 again and in the direction of the C-arm 7.

Figure 2:
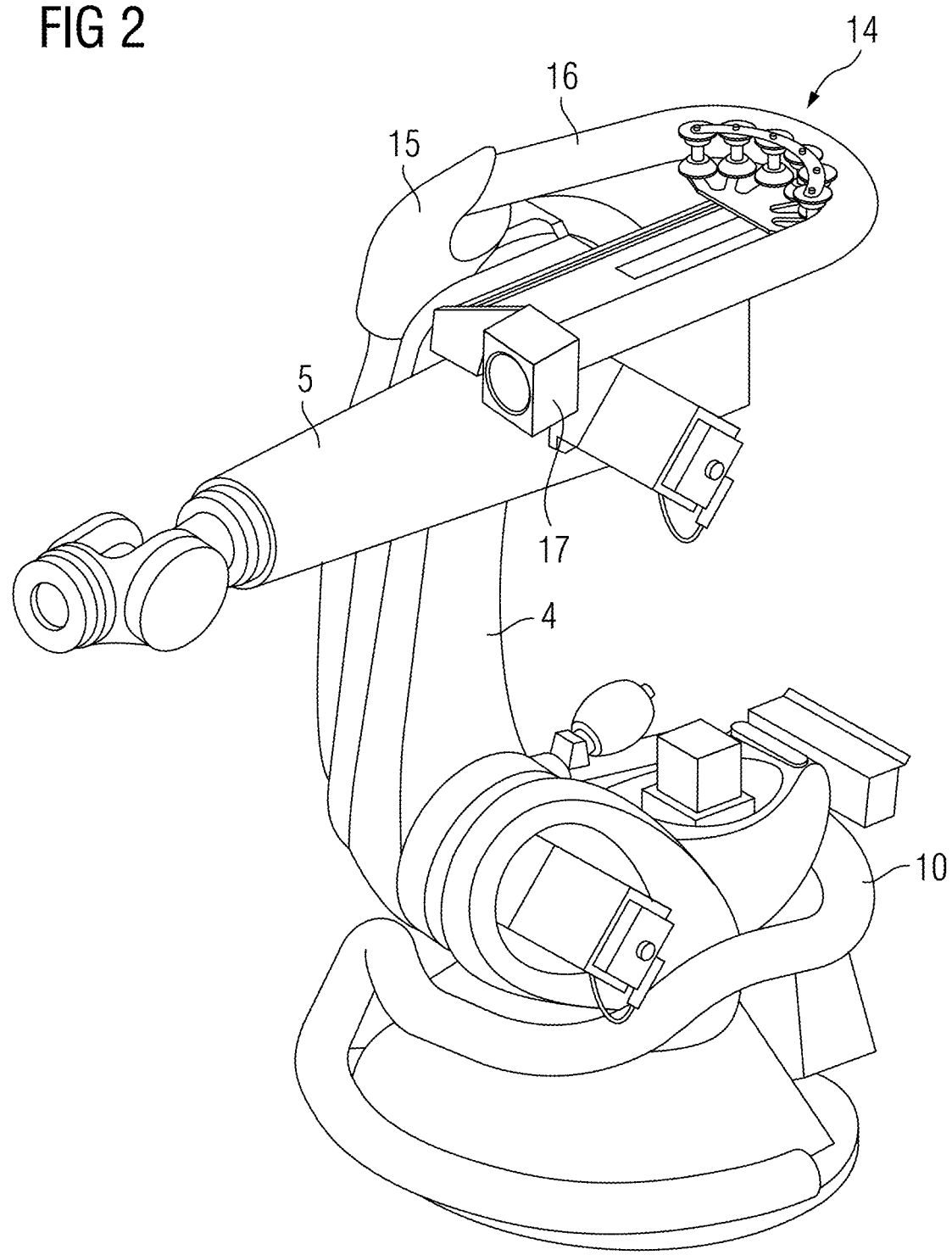
FIG. 2 shows an embodiment of the examination and/or treatment device from FIG. 1 without cladding parts.

FIG. 2, in which inter alia the housing 13 is not shown, shows an articulation piece 15 into which the cladding tube 10 runs and to which it is connected to the extent that the cladding tube 10 can turn relative to the articulation piece 15, in other words can align about its longitudinal axis therefore. The articulation piece 15 then merges into a guide tube 16, which has a U-shape and is flexible. It is made for example from PMA just like the cladding tube 10.

At its other end the flexible guide tube 16 has a further articulation piece 17, wherein the cladding tube 10 together with the cables exits at this end. It is likewise connected to the articulation piece 17 in such a way that it can be rotated about its longitudinal axis, in other words it can align relative to the articulation piece 17 therefore, so any rotations resulting in space during a movement of the C-arm 7 can be compensated hereby.

Figure 3:
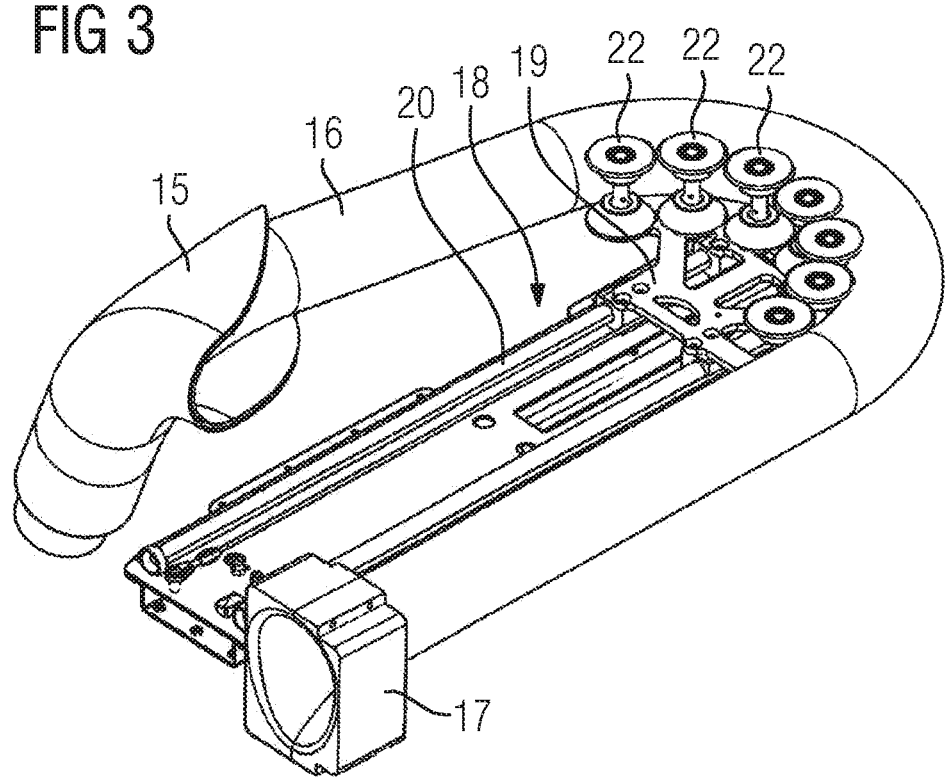
FIG. 3 shows an enlarged detailed view of the carriage arrangement.

The guide tube 16 runs over a carriage arrangement 18, and this is shown enlarged in FIG. 3. The carriage arrangement 18 comprises a carriage 19, which is arranged so as to be linearly movable on a carriage holder 20, which is connected to the articulated arm 5. The carriage 20 can be moved against the restoring force of two restoring elements 21 (see FIG. 4). A plurality of deflection rollers 22 is arranged on the carriage, and these are positioned in an arcuate shape or semicircular shape, and around which rollers the guide tube 16 is guided.

In the assembled position, the cladding tube 10 is connected to the C-arm 7, the leads are of course guided accordingly to the equipment secured to the C-arm 7. If the C-arm 7 is now moved in space, and this can occur in the form of a translatory and/or rotational movement, a tension is exerted on the cladding tube 10 in the process. This tension, owing to the coupling to the guide tube 16, is passed on to this tube, which, owing to its flexibility, is moved with the cladding tube 10, with this movement occurring against the restoring force, which is built up by the restoring elements 21 in the form of the illustrated gas springs. The carriage 19 is therefore moved along the support 20, the flexible guide tube 16 runs around the deflection rollers 22 and the cladding tube 10 including the leads is pulled out of the lead store. If the tension is relaxed again, the restoring force of the restoring elements 21 resets the carriage 19 again, in other words the guide tube 16 is retracted or pushed back again. This ensures that the cladding tube 10 is ultimately always retracted sufficiently far such that it does not randomly run, or rather hang, in space, in particular in the region in which it runs to the C-arm 7.

Figure 5:
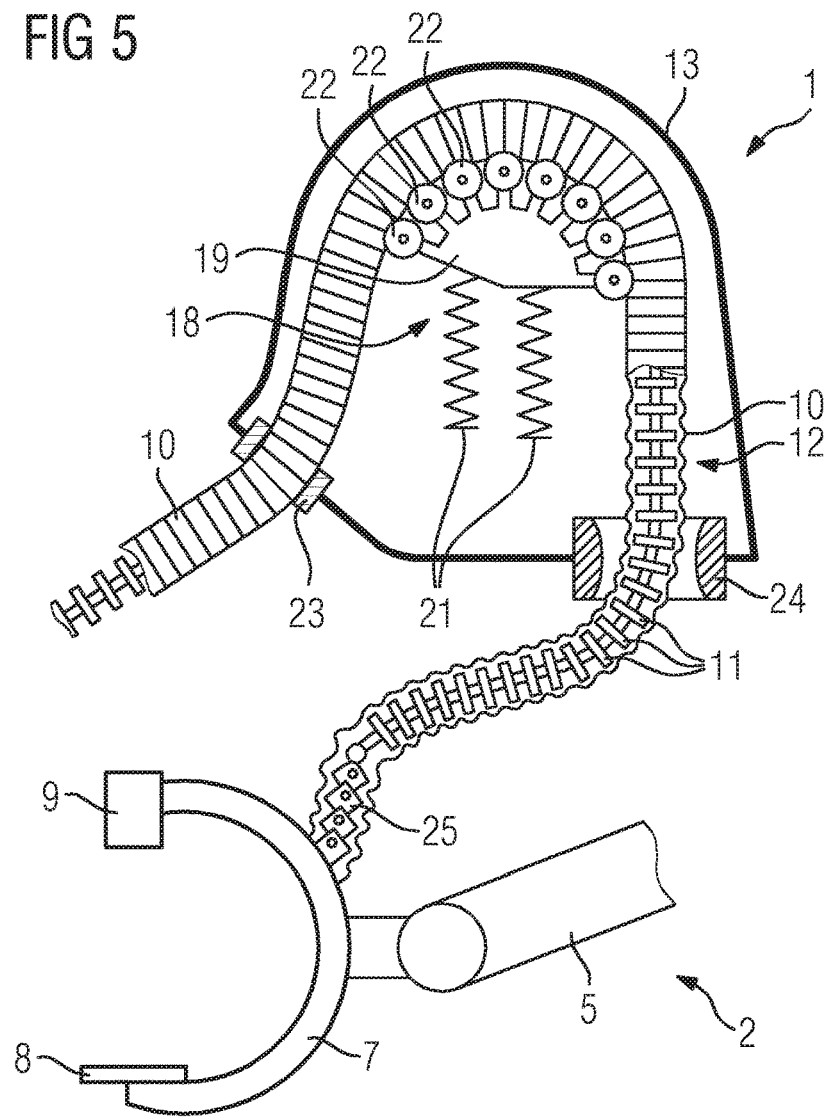
FIG. 5 shows a schematic illustration of an inventive examination and/or treatment device of a second embodiment.

FIG. 5 shows a schematic illustration of an inventive examination and/or treatment device 1 of a second embodiment, with identical reference characters being used for identical components.

A multi-axis robot 2 is also provided here, of which only a part in the form of the articulated arm 5 is shown, and this is coupled to the C-arm 7, which in turn supports the radiation source 8 and the radiation receiver 9.

The housing 13 having the carriage arrangement 18 provided therein is also shown, comprising the carriage 19, which can be linearly moved against the restoring force, formed by two restoring elements 21, on the carriage holder (not shown here). A series of deflection rollers 22 is also provided here on the carriage 19.

Also shown is the cladding tube 10 and the energy chain 12 already described in which the leads are received, which energy chain 12 runs through the cladding tube 10.

In this embodiment the cladding tube 10 is coupled by a clamping element 23 or articulated element on the input housing 13 to this housing but is also rotatably connected here. At the output of the housing 13 is provided just one outlet part 24, through which the cladding tube 10 runs but to which it is not connected. As FIG. 5 shows, in this embodiment namely the cladding tube 10 itself runs directly over the carriage arrangement 18, or rather over the deflection roller 22. This means that the carriage is actuated directly via the cladding tube 10 if the C-arm 7 is moved in space.

The cladding tube 10 itself runs directly to the C-arm 7, and is therefore connected to it there, so the appropriate tension can be exerted.

A connection of the energy chain 10 to a metallic member protection chain 25, which is used as kink protection, and which for its part is fixed to the C-arm 7, is also shown. A metallic member protection chain 25 of this kind as well as the energy chain 10 of course is also preferably provided in the embodiment according to FIGS. 1-4.

Figure 6:
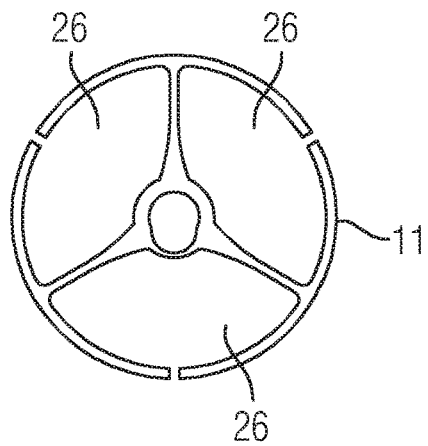
FIG. 6 shows an illustration of an element of an energy chain comprising a plurality of chambers.

FIG. 6 shows finally an element 11 of the energy chain 12, which, as described, comprises a plurality of such elements 11, which are movably coupled together. In the illustrated example each element 11 has three chambers 26 through which the leads of whatever kind are guided. This provides a series of possibilities. Firstly, the energy chain provides tension relief over the entire length of the lead assembly since a possible mechanical load is located on the energy chain 12 but not on the leads. The distribution of the leads in the corresponding chambers 26 provides the advantage that there is no uncontrolled crossing of the leads since they do not run loosely as a whole in the cladding tube 10 but are distributed in a structured manner among the chambers 26 of the energy chain 12. This of course also provides corresponding kink protection at all points of the lead strand.

Furthermore, the retracting force is primarily introduced by the energy chain 12 and the cladding tube 10; the leads are not involved in this or only to a negligible extent.

Coupling of the energy chain 12 to the metallic member protection chain 25 finally provides very good directional guidance of the application of force at the C-arm input.

Overall, at least one embodiment of the invention proposes an examination and/or treatment device, which allows safe and reliable guidance of the leads to the corresponding equipment on the C-arm without these leads running or hanging in space in an uncontrolled manner. A very compact construction is achieved by provision of the carriage arrangement. This provides a pulley guide with a translation of 2:1 and a multi-roller solution for the deflection of either the guide tube, in which the cladding tube together with the energy chain is guided, or of the cladding tube together with the energy chain itself. A further advantage lies in the arrangement of the carriage arrangement on the multi-axis robot itself, in other words no ceiling installation or the like now has to be provided for the implementation of the lead store, for which the carriage arrangement is used.

The arrangement thereof in the housing provides a simple assembly and service option as well as the ability to be easily cleaned.

Furthermore, there is the possibility of ensuring by way of one or appropriate safety switches that the movement of the robot is terminated immediately if either the maximum withdrawal of the guide tube or cladding tube is reached, or if there are other movement problems in respect of the carriage guidance, etc. Corresponding sensors or switches are provided inside the tensile or movement path for this purpose, and these can detect this movement.

Although the invention has been illustrated and described in detail by the preferred example embodiment, it is not limited by the disclosed examples and a person skilled in the art can derive other variations herefrom without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE CHARACTERS

1 examination and/or treatment device
2 multi-axis robot
3 articulated arm
4 articulated arm
5 articulated arm
6 base
7 C-arm
8 radiation source
9 radiation receiver
10 cladding tube
11 member
12 energy chain
13 housing
14 carriage arrangement
15 articulation piece
16 guide tube
17 articulation piece
18 carriage arrangement
19 carriage
20 carriage holder
21 restoring element
22 deflection roller
23 clamping element
24 outlet part
25 member protection chain
26 chamber

What is claimed is:

1. An examination or treatment device comprising:
    a multi-axis robot including an articulated arm, the articulated arm being movable in space along with leads received in a flexible cladding tube and guidable to one or more other examination or treatment devices arranged on the articulated arm or on a support arranged on the articulated arm, the articulated arm including
        a carriage arrangement including
            a carriage including at least one deflection roller, the at least one deflection roller being linearly displaceable against at least one restoring element configured to build up a restoring force, wherein the flexible cladding tube or a guide tube surrounding the flexible cladding tube is guidable around the at least one deflection roller.

2. The examination or treatment device of claim 1, wherein the at least one deflection roller includes a plurality of deflection rollers, arranged along an arcuate path on the carriage.

3. The examination or treatment device of claim 1, wherein the restoring element is a spring element.

4. The examination or treatment device of claim 3, wherein the spring element is a gas pressure spring, a helical spring or a laminated disk spring.

5. The examination or treatment device of claim 1, wherein the carriage arrangement includes a carriage holder on which at least one linear guide, to guide the carriage, is provided.

6. The examination or treatment device of claim 5, wherein the restoring element is supported on the carriage holder and on the carriage.

7. The examination or treatment device of claim 1, further comprising:
resilient end stops, for damping movement of the carriage into an end position.

8. The examination or treatment device of claim 1, wherein the articulated arm includes
a first arm, movably connected to a base frame, and
a second arm, pivotably connected to the first arm, wherein the carriage arrangement is arranged on the second arm.

9. The examination or treatment device of claim 1, wherein the leads are received in a flexible, multi-membered energy chain, running through the cladding tube.

10. The examination or treatment device of claim 9, wherein the energy chain includes two or more chambers for receiving at least one of the leads.

11. The examination or treatment device of claim 9, wherein the energy chain, an end of the energy chain, facing the examination or treatment device or the support, being secured to the examination or treatment device or the support or a metal member protection chain connected to the examination or treatment device or the support.

12. The examination or treatment device of claim 1, wherein the cladding tube is rotatably connected to the guide tube by at least one articulated connection element.

13. The examination or treatment device of claim 1, wherein the cladding tube is connected by an articulated connection component to the support.

14. The examination or treatment device of claim 1, wherein the support is a C-arm and the examination or treatment device includes a radiation source and a radiation receiver.

15. The examination or treatment device of claim 2, wherein the restoring element is a spring element.

16. The examination or treatment device of claim 15, wherein the spring element is a gas pressure spring, a helical spring or a laminated disk spring.

17. The examination or treatment device of claim 2, wherein the carriage arrangement includes a carriage holder on which at least one linear guide, to guide the carriage, is provided.

18. The examination or treatment device of claim 17, wherein the restoring element is supported on the carriage holder and on the carriage.

19. The examination or treatment device of claim 2, further comprising:
resilient end stops, for damping movement of the carriage into an end position.

20. The examination or treatment device of claim 2, wherein the articulated arm includes
a first arm, movably connected to a base frame, and
a second arm, pivotably connected to the first arm, wherein the carriage arrangement is arranged on the second arm.

21. The examination or treatment device of claim 2, wherein the leads are received in a flexible, multi-membered energy chain, running through the cladding tube.

22. The examination or treatment device of claim 10, wherein the energy chain, an end of the energy chain, facing the examination or treatment device or the support, being secured to the examination or treatment device or the support or a metal member protection chain connected to the examination or treatment device or the support.

* * * * *